United States Patent [19]

Molloy et al.

[11] 4,228,293

[45] Oct. 14, 1980

[54] IODO-A-23187 DERIVATIVES

[75] Inventors: R. Michael Molloy; Manuel Debono, both of Indianapolis, Ind.

[73] Assignee: Eli Lilly and Company, Indianapolis, Ind.

[21] Appl. No.: 950,486

[22] Filed: Oct. 11, 1978

[51] Int. Cl.$^2$ .................... C07D 493/10; A61K 31/42
[52] U.S. Cl. .................................... 548/216; 548/104; 424/272; 252/184
[58] Field of Search .................. 260/307 D; 548/216, 548/104

[56] References Cited

U.S. PATENT DOCUMENTS

| | | | |
|---|---|---|---|
| 3,873,715 | 3/1975 | Pressman | 424/283 |
| 3,923,823 | 10/1975 | Gale et al. | 260/307 D |
| 3,944,573 | 3/1976 | Westley | 424/285 |
| 3,960,667 | 6/1976 | Gale et al. | 195/80 R |

OTHER PUBLICATIONS

Chaney et al., J. Antibiotics, 27, 424 (1976).

*Primary Examiner*—Mark L. Berch
*Attorney, Agent, or Firm*—Nancy J. Harrison; Arthur R. Whale

[57] ABSTRACT

Iodo-A-23187 derivatives, prepared by reaction of antibiotic A-23187 with iodine monochloride, and salts thereof, which are (1) useful biochemical tools for the study of transport of ions in cellular systems and (2) useful chemical tools for removal of recovery of ions.

3 Claims, No Drawings

IODO-A-23187 DERIVATIVES

BACKGROUND OF THE INVENTION

1. Field of the Invention

Antibiotic A-23187 is a unique polyether antibiotic having the following structure

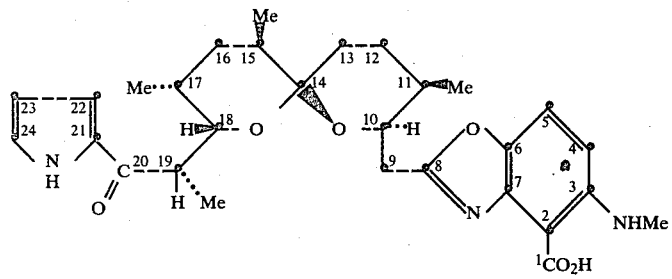

The numbering system used herein for A-23187 is that proposed by M. O. Chaney, Noel D. Jones and Manuel Debono in J. *Antibiotics* 29 (4), 424–427 (1976).

In Westley's review on polyether antibiotics, he classifies ionophores by chemical structure [see J. W. Westley in "advances in Applied Microbiology," Vol. 22, D. Perlman, Ed., Academic Press, New York, N.Y., 1977, pages 177–223]. Using Westley's classification, there are four types of ionophore antibiotics: (1) polyethers; (2) peptides; (3) cyclodepsipeptides; and (4) macrotetrolides. Within the polyether subclass, there are four subgroups: 1(a) monovalent polyethers (e.g., monensin, nigericin); 1(b) monovalent monoglycoside polyethers (e.g., dianemycin); 2(a) divalent polyethers (e.g., lasalocid, lysocellin) and 2(b) divalent pyrrole ethers (e.g., antibiotic A-23187). To date, antibiotic A-23187 is the only known member of this last group.

Ionophore A-23187 has proven to be a powerful and unique research tool to investigate $Ca^{2+}$-dependent control mechanisms in a large variety of cellular systems. Calcium ($Ca^{2+}$) ion is widely recongized as an intracelluar "second messenger" [H. Rasmussen and D. P. B. Goodman, *Physiological Reviews* 57 (3), 421–509 (1977)]. The mechanisms by which $Ca^{2+}$ controls cellular excitation phenomena appear similar to, and linked to, control by cyclic nucleotides and prostaglandins.

Of approximately 100 known, naturally occurring ionophores, A-23187 is one of three which are able to transport divalent cations significantly. A-23187 is the only inonophore substantially selective for the transport of divalent over monovalent cations.

Despite this unique utility, A-23187 is not an ideal $Ca^{2+}$ ionophore from a physiological viewpoint. It transports $Mg^{2+}$ with a similar efficiency to $Ca^{2+}$, and its discrimination for divalent over monovalent cations is not complete [D. R. Pfeiffer and H. A. Lardy, *Biochemistry* 15, 935 (1976)].

2. The Prior Art

Halo derivatives of the polyether antibiotics lasalocid A (antibiotic X-537A; U.S. Pat. No. 3,873,715) and iso-lsalocid A (U.S. Pat. No. 3,944,573) are known. The complex structure of antibiotic A-23187, however, precludes any a priori prediction of the site(s) of halogenation.

BRIEF SUMMARY OF THE INVENTION

We have discovered specific iodo derivatives of A-23187 having unique ionophorous activity. The compounds of our invention are selected from a group consisting of the following:

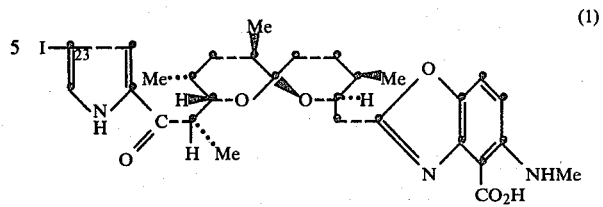

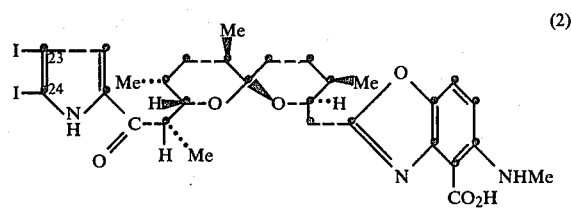

and the salts of (1) and (2). As is the case with antibiotic A-23187, when the compounds of this invention form salts with divalent cations, these salts contain two molecules of A-23187 derivative per molecule of metal ion. Such salts are frequently referred to as complexes.

Chemical names for the compounds of formulas (1) and (2) are as follows:

| Compounds of Formula | Name |
|---|---|
| (1) | 5-(methylamino)-2-[[3β,9α,11β-trimethyl-8-[1α-methyl-2-oxo-2-(4-iodo-1H-pyrrol-2-yl)ethyl]-1,7-dioxaspiro[5.5]undec-2β-yl]methyl]-4-benzoxazolecarboxylic acid |
| (2) | 5-(methylamino)-2-[[3β,9α,11β-trimethyl-8-[1α-methyl-2-oxo-2-(4,5-diiodo-1H-pyrrol-2-yl)ethyl]-1,7-dioxaspiro[5.5]undec-2β-yl]methyl]-4-benzoxazolecarboxylic acid. |

For convenience herein, these compounds will be identified as A-23187 derivatives as follows:

| Compounds of Formula | Name |
|---|---|
| (1) | 23-iodo-A-23187 |
| (2) | 23,24-diiodo-A-23187 |

The compounds of the present invention are prepared by reacting A-23187 (as a dimeric complex with a divalent cation) with iodine monochloride (ICl) under acidic conditions.

The compounds of this invention have a unique effect on ion transport and are, therefore, new tools for the study of cation binding and transport selectivity patterns for divalent and monovalent cations of biochemical importance. Such tools are important, for example, for the study of (1) mechanisms regulating intracellular ionic distributions and concentrations and (2) the involvement of the intracellular ionic environment in the regulation of cellular functions, especially those of a contractile or secretory nature.

Furthermore, the compounds of this invention provide new tools for the selective chemical removal of particular cations.

DETAILED DESCRIPTION OF THE INVENTION

The compounds of this invention are prepared from antibiotic A-23187. Antibiotic A-23187 can be prepared by culturing the microorganism *Streptomyces chartreusis* Calhoun and Johnson NRRL 3882 and then isolating antibiotic A-23187 as described by Gale et al. in U.S. Pat. Nos. 3,923,823 and 3,960,667.

The compounds of this invention are prepared by reacting antibiotic A-23187 with iodine monochloride in an acidic solution, such as acetic acid. Generally, a dimeric complex of A-23187 with a divalent cation is used. These dimeric complexes can be represented by the abbreviation "$A_2$-M" wherein A represents the A-23187 moiety and M represents the metal cation. The product of the reaction is, because of the acidic environment, in the free acid form.

The compound of formula (1) is prepared when the reaction period is short (such as, for example, about 30 minutes at room temperature) and the molar ratio of ICl to A-23187 is lower (e.g., 2:1). The compound of formula (2) is prepared when the reaction period is longer (such as, for example, about 60 minutes at room temperature) and the molar ratio of ICl to A-23187 is greater (e.g., 4:1). Salts of the compounds of formulas (1) and (2) can be prepared from the corresponding free acid by conventional chemical methods.

The compounds of formulas (1) and (2) and the salts of these compounds are included within our invention. The salts are useful for solubilizing cationic species in nonaqueous solvents. Among these salts, salts which are "pharmaceutically acceptable" are a preferred group since they are especially amenable for involvement in studies of the transport of ions in cellular systems. "Pharmaceutically acceptable" salts are those salts in which the toxicity of the compound as a whole toward warm-blooded animals is not increased relative to the non-salt form.

Representative and suitable salts of the compounds of formulas (1) and (2) include those salts formed with divalent and monovalent cations. Alkaline-earth salts, alkali-metal salts and transition-metal salts are among the suitable salts contemplated by this invention. Typical useful divalent cations for salt (complex) formation include magnesium, calcium, manganese, cadmium, barium, iron, zinc, lead, mercury and the like. Typical monovalent cations for the preparation of useful salts include sodium, potassium, lithium, and the like.

The compounds of this invention are useful antibacterial agents. In this aspect, these compounds may be used in the same manner in which the parent antibiotic is used, as described in U.S. Pat. No. 3,923,823. A bioassay for the antibacterial activity of A-23187 has been described by J. E. Westhead in *Antimicrobial Agents and Chemotherapy* 11 (5), 916–918 (1977). The test organism for this bioassay is *Staphylococcus aureus* (H-Heatley strain, NRRL B-314). Table I summarizes the results of typical compounds of this invention using this bioassay.

TABLE I

| Compound | Bioassay (mcg/ml) |
| --- | --- |
| 23-iodo-A-23187 (free acid) | 1331 |
| 23,24-diiodo-A-23187 (free acid) | 560 |
| A-23187 (free acid) | 1060 |

The compounds of the present invention are, in general, less toxic than the parent antibiotic. Table II summarizes the acute toxicities of representative compounds in mice, expressed as $LD_{50}$, when the compounds are administered intraperitoneally.

TABLE II

| Compound | $LD_{50}$(mg/kg × 1) |
| --- | --- |
| 23-iodo-A-23187 (free acid) | 25 |
| 23,24-diiodo-A-23187 (free acid) | 100 |
| A-23187 (free acid) | 5.8 |

In a more important aspect, the compounds of this invention exhibit ion-binding and ion-transport properties and are, therefore, ionophores (ion-bearers) (see B. C. Pressman, Alkali Metal Chelators—The Ionophores, in "Inorganic Biochemistry," Volume 1, G. L. Eichhorn, Elsevier, (1973). Such compounds can be used when the selective removal of a particular cation is desired. Examples of such uses include the removal and recovery of silver ions from solutions in photography, the removal of toxic cations from industrial waste streams before such streams are discharged to the environment, and deionization of sea water. A compound of this invention can be used as one component of an ion-specific electrode (see O. Kedem, et al., U.S. Pat. No. 3,753,887). These compounds alter the cation permeability of both natural and artificial membranes. A compound of this invention can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, *Science* 172, 377 (1971)].

In yet another aspect, the compounds of this invention are active as inhibitors of the enzyme ATPase. ATPase, an alkali-metal-sensitive enzyme found in cell membranes, is involved in the energy necessary for active transport. "Active transport" refers to the energy-requiring series of operations whereby intracellular and extracellular fluids maintain their compositions. Inhibitors of ATPase reduce the energy required for active transport. Table III summarizes the results of in vitro tests measuring inhibition of cation transport ATPase in liver mitochondria [measured as half effective concentration (Ic50) in mcg/ml].

TABLE III

| Compound | ATPase Induced By | |
| --- | --- | --- |
| | $K^+$ monazomycin | $CaCl_2$ |
| 23-iodo | | |

TABLE III-continued

| Compound | ATPase Induced By | |
|---|---|---|
| | K+ monazomycin | CaCl₂ |
| A-23187 | <0.05 | 5 |
| 23,24-diiodo-A-23187 | 0.8 | — |
| A-23187 | 0.5 | 0.5 |

In order to illustrate this invention more fully, the following examples are provided.

EXAMPLE 1

23-Iodo-A-23187 Free Acid

A-23187 Mg$^{++}$ complex (534 mg, 0.5 mmol) was dissolved in glacial acetic acid (20 ml) containing 1 ml of 1 N HCl. Iodine monochloride (162 mg, 1.0 mmol) was added to this solution. The deep violet colored reaction mixture was stirred for 30 minutes at room temperature and then poured onto ice/water (300 ml). The resulting solution was extracted 3 times with CHCl₃. The combined extracts were washed sequentially with water, 2% aqueous Na₂SO₃ solution, water, 0.1 N HCl solution, and water. The organic layer was dried over Na₂SO₄ overnight and then concentrated in vacuo to give 612 mg of yellow foam. This foam (a 2-3 spot mixture) was chromatographed over citric-acid-impregnated silica gel (CASG, Woelm, 70-150 mesh; 350 g) to give 556 mg of foam. This foam was dissolved in CHCl₃, washed with water, dried over Na₂SO₄ overnight and concentrated under vacuum. The concentrate was crystallized from ether:petroleum ether (1:4) to give 287 mg of 23-iodo-A-23187 (free acid), melting point 186°–188°. (44% yield).

$[\alpha]_D^{25}$ +9.9° (c 0.021, CH₃OH); $\lambda_{max}$(CH₃OH) 226 ($\epsilon$ 26,695), 253 ($\epsilon$ 13,800), 299 ($\epsilon$ 11,500), and 375 nm ($\epsilon$ 7,800); ¹H NMR (CDCl₃, 100 MHz, 6–8 ppm region) pyrrole protons: 698 (m) and 7.08 ppm (m); D₂O exchange gave doublets (J=1.5 cps); benzoxazole protons: 6.61 (d) and 7.54 ppm (d, J=9 cps).

Analysis Calcd. for C₂₉H₃₆IN₃O₆: C, 53,63; H, 5.59; N, 6.47; I, 19.54. Found: C, 53.76; H, 5.66; N, 6.24; I, 19.57.

EXAMPLE 2

23,24-Diiodo-A-23187 Free Acid

A-23187 Mg$^{++}$ complex (534 mg, 0.5 mmol) was dissolved in glacial acetic acid (20 ml) containing 1 ml of 1 N HCL solution. ICl (324 mg, 2.0 mmol) was added to this solution. After allowing the reaction mixture to stand for 60 minutes at room temperature in the dark, the resulting violet solution was poured onto ice/water (300 ml). The workup procedure used in Example 1 was followed to give 642 mg of crude 23,23-diiodo-A-23187 free acid. This was chromatographed over 350 g of CASG as described in Example 1 to give 280 mg of foam. The foam was dissolved in CHCl₃. The resulting CHCl₃ solution was washed with water, dried over Na₂SO₄ overnight, and evaporated under vacuum to give 178 mg of 23,24-diiodo A-23187 free acid as a foam. (23% yield).

$[\alpha]_D^{25}$ +22.9° (c 2, CH₃OH); $\lambda_{max}$ (CH₃OH) 220 ($\epsilon$ 27,200), 250 ($\epsilon$ 11,000), 308 ($\epsilon$ 14,276), and 365 nm ($\epsilon$ 5,500); ¹H NMR (CDCl₃, 100 MHz, 6–8 ppm region, pyrrole proton: 6.94 ppm (br d, J=3.5 cps) collapses to a singlet on exchange with D₂O; benzoxazole protons: 6.66 (d) and 7.59 ppm (d, J=9 cps). M.S.: M/e 775, 346, 318, 206.

We claim:

1. A compound selected from a group consisting of the following:

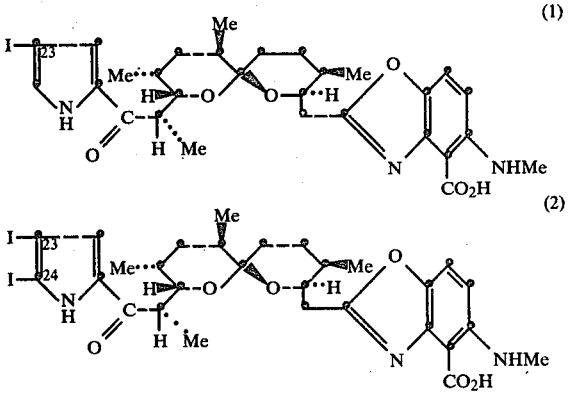

and the pharmaceutically acceptable cationic salts of (1) and (2).

2. A compound of claim 1 having formula (1) and the pharmaceutically acceptable cationic salts of (1).

3. A compound of claim 1 having formula (2) and the pharmaceutically acceptable cationic salts of (2).

* * * * *